US005596996A

United States Patent [19]

[11] Patent Number: 5,596,996

[45] Date of Patent: Jan. 28, 1997

Johanson et al.

[54] HIGH SUPPORT NITINOL TUBE GUIDEWIRE WITH PLASTIC PLUG TRANSITION

[75] Inventors: Mark A. Johanson, Littleton, Mass.; Michael S. Noone, Londonderry, N.H.

[73] Assignee: Medtronic, Inc., Minneapolis, Minn.

[21] Appl. No.: 413,524

[22] Filed: Mar. 30, 1995

[51] Int. Cl.$^{6}$ .......... A61B 5/00

[52] U.S. Cl. .......... 128/772; 128/657

[58] Field of Search .......... 128/722, 657; 604/164, 281

[56] References Cited

U.S. PATENT DOCUMENTS

| | | | |
|---|---|---|---|
| 3,789,841 | 2/1974 | Antoshkiw | 128/2.05 |
| 4,884,579 | 12/1989 | Engelson | 128/772 |
| 4,925,445 | 5/1990 | Sakamoto et al. | 604/95 |
| 5,067,489 | 11/1991 | Lind | 128/772 |
| 5,069,226 | 12/1991 | Yamauchi et al. | 128/772 |
| 5,176,149 | 1/1993 | Grenouillet | 128/772 |
| 5,243,996 | 9/1993 | Hall | 128/772 |
| 5,452,726 | 9/1995 | Burmeister et al. | 128/772 |

OTHER PUBLICATIONS

55–*Nitinol–The Alloy with a Memory: Its Physical Metallurgy, Properties, and Applications,* by Jackson et al., 1972, Prepared under contract for NASA. Foreword, pp. 1–2, p. 1037.

*Primary Examiner*—Max Hindenburg
*Assistant Examiner*—Pamela L. Wingood
*Attorney, Agent, or Firm*—Dianne M. F. Plunkett; Harold R. Patton

[57] ABSTRACT

A catheter guidewire having an elongate core wire, an elongate tube defining a tube lumen, the proximal end of the tube being affixed to the distal end of the core wire. The tube has a smooth exterior surface and one or more plug segments filling the tube lumen, each plug segment having a stiffness less than that of the core wire and less than that of the proximally preceding plug segment. The proximal end of the proximal most plug segment is affixed to the distal end of the core wire, the distal end of the tube is affixed to the distal most plug segment. A smoothly rounded distal tip extends beyond and is affixed to the distal end of the tube. The tube may be formed of a super-elastic metallic member or formed from a synthetic resin. The tube wall thickness is preferably between 0.002 inches and 0.005 inches.

19 Claims, 1 Drawing Sheet

20 25 35 60 80 85 65 30 70 50 75 45 40

HIGH SUPPORT NITINOL TUBE GUIDEWIRE WITH PLASTIC PLUG TRANSITION

FIELD OF THE INVENTION

The present invention relates to guidewires, and more particularly, to high support guidewires with a flexible tube at the distal end. Such a guidewire can be used in PTCA procedures such as balloon angioplasty, atherectomy, stent implantation procedures, or radiology procedures.

BACKGROUND OF THE INVENTION

One of the therapeutic procedures applicable to the present invention is known as percutaneous transluminal coronary angioplasty (PTCA). This procedure can be used, for example, to reduce aerial build-up of cholesterol fats or atherosclerotic plaque. Typically a guidewire is steered through vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The original catheter can then be withdrawn and a catheter of a different size or another device such as an atherectomy device can be inserted.

The major considerations in guidewire design include steerability, flexibility, medial stiffness or support, bending in transition areas, tip formability and radiopacity. In a typical guidewire construction a tapered stainless steel core wire has a platinum spring coil wound around the tapered distal end of the core wire. The tapered area of the core wire is called the transition segment. The longer the tapered transition segment, the more flexible the guidewire. A blunt tip is typically welded to the distal end of the guidewire to reduce trauma to the blood vessel.

Support refers to a guidewire's ability to provide a strong "platform" or track for the catheter to move over as it is crossing the lesion. Support becomes crucial when the lesion is tight. Catheters are soft and rely heavily on the support provided by the guidewire. The spring coil is typically used to provide device support and maintain a consistent guidewire outer diameter. If the outer diameter of the guidewire is reduced, it will exert more force per unit area and may result in cutting through the blood vessel rather than tracking through the bends in the vessels. Increasing core wire diameter also assists in providing enhanced support. The spring coil wire is wound into a coil and placed over the core wire. The spring coil proximal end is difficult to attach to the core wire. A typical spring coil is approximately 0.002 inches in diameter thereby providing a very small area with which to attach to the core wire. Spring coil guidewire construction has been known in the art for many years. An early example of such guidewire construction includes U.S. Pat. No. 3,789,841 for a "Disposable Guide Wire" to Antoshkiw.

Transition refers to areas of changing diameter along the guidewire. A smooth transition gives the guidewire the ability to follow itself smoothly around vascular bends. If a stiffer portion of the guidewire behind the flexible tip does not follow the tip around vascular bends, the tip position may be lost. A guidewire with poor or rough transition will show elbows or bends in the vascular curves. Without smooth transitions a guidewire will not corner smoothly. Smooth transitions also facilitate the tracking of the balloon catheter over the wire when crossing the lesion.

U.S. Pat. No. 4,884,5791 to Engelson for "Catheter Guidewire" discloses a guidewire with proximal, intermediate and distal sections. The intermediate section has greater lubricity than the adjacent proximal and distal sections. The greater frictional coefficient in the distal end segment acts to anchor the end of the wire in a branch vessel when the guide wire has been advanced across the sharp-bend vessel junction. In FIG. 6, the distal segment of the core wire is incased in a polymer tube having a series of annular grooves to provide increased tube flexibility as well as greater frictional coefficient.

Elastomers and shape memory materials have been used in the catheter industry to promote elasticity and to promote tips that will return to a preformed curve after flexing. Super-elastic guidewires are known in the art, as for example, U.S. Pat. No. 4,925,445, to Sakamoto et al. for "Guide Wire for Catheter" which discloses a guidewire with at least portions of the inner core formed of the super-elastic metallic member. U.S. Pat. No. 5,067,489 to Lind for "Flexible Guide with Safety Tip" discloses an elongated, helically wound coil and an elongated flexible metal core of shape memory alloy. U.S. Pat. No. 5,069,226 to Yamauchi et al. for "Catheter Guidewire with Pseudo Elastic Shape Memory Alloy" discloses a catheter guide wire comprising a solid core wire of Ti-Ni shape memory alloy and an outer jacket coveting the core wire. The jacket is made of any one of synthetic resins such as polyethylene, polyvinylchloride, polyester, polypropylene, polyamide, polyurethane, polystyrene, fluoride resin, silicone rubber, and other elastomers. U.S. Pat. No. 5,243,996 to Hall for "Small-Diameter Superelastic Wire Guide" discloses a mandrel of metallic superelastic material, such as nitinol having a smoothly rounded tip attached to the distal tip of the mandrel and a coil attached at the distal region of the mandrel, the coil coaxially surrounding a portion of the distal region.

SUMMARY OF THE INVENTION

A drawback of spring coils as currently used in guidewires is that their indented surface may not pass through tight lesions effectively and may catch on devices being passed over them such as devices with cutting mechanisms. Another disadvantage is that they may provide too much flexibility for some devices to properly track over. Additionally, the spring coil is difficult to manufacture because it requires the wire to be helically wound with a uniform outer diameter, then placed over the core wire and welded thereto. The spring coil is also prone to separation where it attaches. An object of the invention is to eliminate the need of a guidewire spring coil while maintaining a uniform shaft outer diameter and providing sufficient support for more difficult PTCA procedures such as total occlusions, atherectomy, Rotoblator® (a registered trademark of Heart Technology, Inc.) and stent delivery. Another object of the invention is to provide steerability for wire placement. Yet another object of the invention is to avoid attachment weakness at the location where the spring coil would have attached to the core wire.

The above objects and advantages of the present invention, as well as others, are accomplished by providing a catheter guidewire having an elongate core wire, an elongate tube defining a tube lumen, the proximal end of the tube being affixed to the distal end of the core wire. The tube has a smooth exterior surface and one or more plug segments filling the tube lumen, each plug segment having a stiffness less than that of the core wire and less than that of the proximally preceding plug segment. The proximal end of the proximal most plug segment is affixed to the distal end of the core wire, the distal end of the tube is affixed to the distal most plug segment. A smoothly rounded distal tip extends beyond and is affixed to the distal end of the tube. The tube may be formed of a super-elastic metallic member or formed from a synthetic resin. The tube wall thickness is preferably between 0.002 inches and 0.005 inches.

DETAILED DESCRIPTION OF THE PREFERRED EMBODIMENTS

Figure 1:
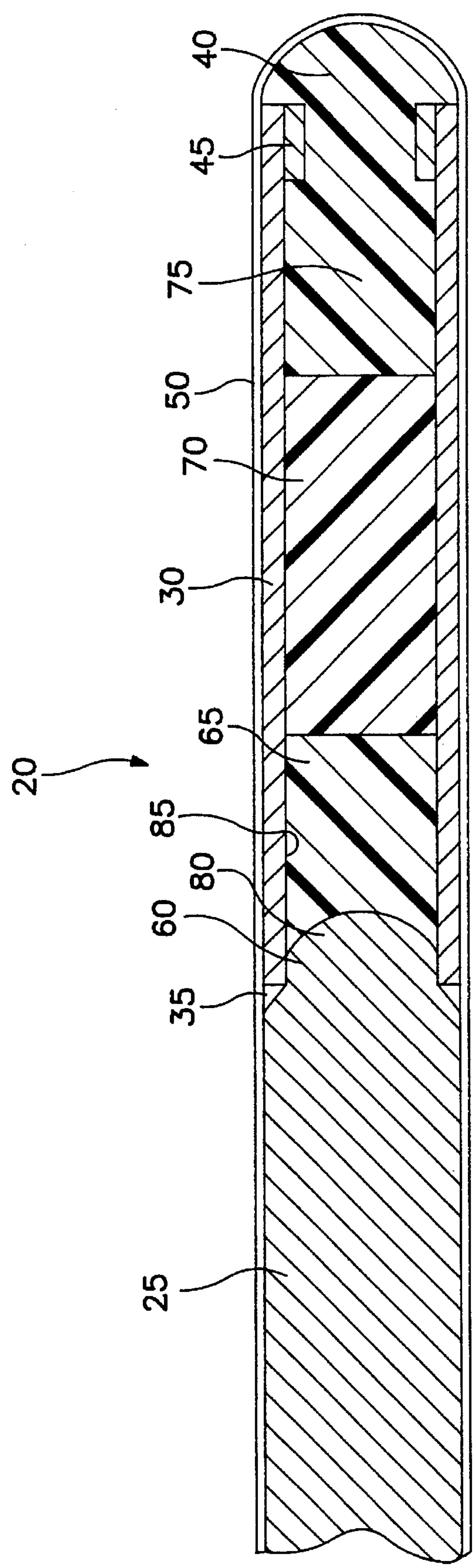
FIG. 1 is an enlarged sectional view of a catheter guidewire according to the invention.

Prior art guidewires are currently constructed with a spring coil over the tapered distal end of the core wire to increase flexibility while maintaining a constant shaft outer diameter. A radiused blunt tip is soldered to the distal end of the core wire and spring coil. Applicant's guidewire 20 is a standard length of 175–310 cm long. Instead of a spring coil, however, applicant's guidewire 20 is constructed using a tube 30 which can be made of an elastomer or an alloy which is highly flexible without permanent deformation such as a shape memory alloy. The tube 30 can be approximately 10 cm to 40 cm long, preferably 30 cm which is the average length from the coronary vessel to the aortic arch. The tube 30 can preferably be made of a shape memory alloy such as nitinol manufactured by Raychem or Forukawa. A preferred embodiment uses NiTi 49–51 atom % Ni.

Shape memory alloys allow one to deform the alloy at a lower temperature with fairly low force and then with merely the application of heat, the material will exert a very strong force as it attempts to regain its previous shape. A useful shape memory alloy property includes an exceptional superelastic springiness if one deforms it at a temperature slightly above the transformation temperature. Shape memory alloys exhibit a very soft, energy absorbing behavior if used just below that temperature.

Examples of shape memory alloys which have a superelastic effect include AgCd 44–49 atom % Cd; AuCd 46.5–50 atom % Cd; CuAlNi 14–14.5 weight % Al, 3–4.5 weight % Ni; CuZn 38.5–41.5 weight % Zn; CuZn X few Weight % X, (X=Si, Sn, Al); InTi 18–23 atom % Ti; NiAl 36–38 atom % Al; NiTi 49–58 atom % Ni; FePt 25 atom % Pt; MnCu 5–35 atom % Cu; FeMnSi 32 weight % Mn, 6 weight % Si.

The use of superelastic NiTi wire has significant advantages over more conventional materials as well as other shape memory alloys. NiTi has a much lower effective modulus than stainless steel. Of the shape memory alloys, the NiTi family is the most commercially attractive system. The NiTi alloy has constituents which are not prohibitively expensive, can be fabricated with existing metalworking techniques and have greater shape memory strain (up to 8%) than other alloys. As seen from the shape memory alloy list supra, many contain expensive or exotic elements which are not as commercially attractive as NiTi.

Tube 30 can also be made of a synthetic resin elastomer such as any one of polyethylene, polyvinyl chloride, polyester, polypropylene, polyamide, polyurethane, polystyrene, and other elastomers. A fluoropolymer can also be used such as TEFLON® from E. I. Du Pont de Nemours & Company, Wilmington, Del. TEFLON® is a form of polytetrafluoroethylene (PTFE). Elastomers are lower cost then shape memory alloys. Shape memory alloys, however, provide more rigidity for better support than most of the elastomers.

The tube 30 is supported by a distally tapering core wire 25. The core wire 25 can be constructed of stainless steel. The tube 30 wall thickness varies depending of the size guidewire 20 used. The bigger the guidewire 20, the thicker the tube 30 must be to provide support. For example, a tube 30 wall thickness of 0.002 inches could be used for 0.010 inch guidewires. A tube 30 wall thickness of 0.005 inches could be used for 0.40 inch guidewires. The preferred tube 30 wall thickness is 0.0025 inches. A constant shaft outer diameter is maintained throughout the tube 30 by step grinding the distal end of the tube to coincide with the core wire tapered step 60.

For example, assume a standard 0.014 inch guidewire with a 30 cm tube 30. An example of a preferred embodiment would contain the following dimensions. The proximal end of the guidewire 20 body would have a substantially uniform diameter of 0.014 inches. The distal end of the core wire 25 would be ground over a length of 5 mm to tapered step 60 with a distal diameter of 0.009 inches. The distal end of the core wire 25 would be formed into a full radius 80 by a means such as grinding. The 5 mm long tapered step 60 is advantageous because it provides a large surface area with which to bond the tube 30 to the core wire 25.

The hollow portions of tube 30 can be plugged with segments of varying durometer plastic segments to create progressively decreasing stiffness toward the distal end of tube 30. Overall stiffness or floppiness can be achieved for different applications. For example, stiffer segments overall would be used for difficult PTCA procedures such as total occlusions, atherectomy, Rotoblator® (a registered trademark of Heart Technology, Inc.) and stent delivery. Floppier segments overall could be used for traversing especially tight lesions.

To achieve variable stiffness, the hollow portions of tube 30 can be plugged with one or more segments of varying durometer plastic such as a synthetic resin elastomer such as any one of polyethylene, polyvinyl chloride, polyester, polypropylene, polyamide, polyurethane, polystyrene, and other elastomers. The proximal end of the proximal most plug segment will be affixed to the radiused distal end 80 of the core wire. The distal most plug segment will be affixed to the tube 30 distal end by an adhesive bond or by a molding process. Adhesives such as cyanoacrylates or epoxy may be used. Those skilled in the art would recognize that any biocompatible adhesive would be satisfactory. The plastic plugs will be molded together after being inserted into the tube 30. Filling the tube 30 with a flexible material will render the tube 30 more kink resistant.

An example of a preferred embodiment would include three plugs of varying durometer plastic. Those skilled in the art would recognize that other numbers of plugs could be used. An acceptable three plug configuration includes the following combination of plug hardnesses and lengths. A material of Shore 75 D can be used for the approximately 10 cm long high durometer plug 65. A material of Shore 55 D can be used for the approximately 20 cm long medium durometer plug 70. A material of Shore 35 D can be used for the approximately 5 cm long low durometer plug 75. Procedures requiring high overall stiffness could be implemented using a material of a Shore 100 D for the approximately 20 cm long high durometer plug 65, a Shore 75 D material for the approximately 10 cm long medium durometer plug 70 and a Shore 55 D material approximately 3 cm long for the low durometer plug 75. Procedures requiring low overall stiffness could be implemented using a Shore 55 D material for the approximately 10 cm long high durometer plug 65, a Shore 40 D material for the approximately 10 cm long medium durometer plug 70, and a Shore 25 D material for the 15 cm long low durometer plug 75.

The proximal end of the tube 30 is affixed to the core wire 25 with an adhesive 35 at the proximal end of the first tapered step 60. Adhesives such as cyanoacrylates or epoxy may be used for joining the tube 30 to the core wire 25. Those skilled in the art would recognize that any biocompatible adhesive would be satisfactory. The present invention avoids the spring coil proximal end attachment problems of the prior art. A typical spring coil is approximately 0.002 inches in diameter thereby providing a very small area with which to attach to the core wire. The tube 30 of the present invention provides a 360 degree area of attachment to the core wire 25. The larger surface area provides for a more reliable attachment.

A tip 40 is formed out of the plastic material extending from the distal end of the low durometer plug 75. Tip 40 is radiused for an atraumatic tip. A radiopaque marker band 45 can be placed in the distal inner lumen of the tube 30 approximately 1–2 cm from the tip 40 enabling the physician to visualize the progress of the tip 40 under fluoroscopy. The marker band 45 can be attached by heat bonding or with an adhesive such as epoxy. Alternatively, having two radiopaque areas would give the physician a sense of scale. The medium durometer plug 70 or the low durometer plug 75 could be made of multiple segments with one of the segments made of plastic loaded with radiopaque fillings. Alternatively, either the medium durometer plug 70 or the low durometer plug 75 could be entirely made of plastic loaded with radiopaque fillings.

After attaching the tube 30 to the core wire 25, the guidewire 20 is coated with a lubricous coating 50 to enhance the movement of devices over it. The guidewire can be coated with a silicone oil or a hydrophilic coating. The advantage of Silicone is that it is inexpensive and easy to apply. The advantage of a hydrophilic coating is that it absorbs moisture and becomes slippery when inserted into the blood stream.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|---|---|
| 20 | Guidewire |
| 25 | Core Wire |
| 30 | Flexible Tube |
| 35 | Adhesive |
| 40 | Tip |
| 45 | Radiopaque Marker Band |
| 60 | Tapered Step |
| 65 | High Durometer Plug |
| 70 | Medium Durometer Plug |
| 75 | Low Durometer Plug |
| 80 | Full Radius |
| 85 | Tube Lemen. |

What is claimed is:

1. A guidewire for use in a catheter comprising:

an elongate core wire having a uniform outer diameter, a proximal end and a distal end;

an elongate tube defining a tube lumen, the tube having the same outer diameter as the core wire, the tube having a proximal end and a distal end, the proximal end of the tube being affixed to the distal end of the core wire, the tube having a smooth exterior surface;

two or more plug segments, each plug segment having the same uniform outer diameter as each other along their length, the plug segments filling the tube lumen, each plug segment having a proximal end and a distal end, each plug segment having a stiffness less than that of the core wire and less than that of the proximally preceding plug segment, the proximal end of the proximal most plug segment being affixed to the distal end of the core wire, the distal end of the tube being affixed to the distal most plug segment; and a smoothly rounded distal tip extending beyond and affixed to the distal end of the tube.

2. The guidewire of claim 1 wherein the core wire tapers down toward the distal end.

3. The guidewire of claim 1 wherein the distal end of the core wire forms a spherically shaped full radius.

4. The guidewire of claim 1 wherein the tube has a constant outer diameter throughout.

5. The guidewire of claim 1 wherein the tube is formed of an elastomer selected from a group of synthetic resins consisting of polyethylene, polyvinyl chloride, polyester, polypropylene, polyamide, polyurethane, polystyrene and polytetrafluoroethylene.

6. The guidewire of claim 1 wherein the tube is formed of a super-elastic metallic material.

7. The guidewire of claim 1 wherein the tube is formed of a super-elastic metallic member including an alloy selected from the groups consisting of NiTi alloy consisting essentially of 49–58 atom % Ni and the balance substantially Ti, CuZn alloy consisting essentially of 38.5–41.5 weight % Zn and the balance substantially Cu, CuZnX, consisting essentially of few weight % X, (X=Si, Sn, Al), NiAl alloy consisting essentially of 36–38 atom % Al and the balance substantially Ni, CuAlNi 14–14.5 weight % Al, 3–4.5 weight % Ni, MnCu 5–35 atom % Cu, FeMnSi 32 weight % Mn, 6 weight % Si.

8. The guidewire of claim 1 wherein the tube has a wall thickness of between about 0.002 inches and 0.005 inches.

9. The guidewire of claim 1 wherein the plug segments are affixed by molding together the distal end of the proximally preceding plug segment with the proximal end of the distally following plug segment.

10. The guidewire of claim 1 having a high durometer plug segment with a proximal end and a distal end, a medium durometer plug segment with a proximal end and a distal end and a low durometer plug segment with a proximal end and a distal end, the high durometer plug segment having a hardness of about Shore 55 D to 100 D, the medium durometer plug segment having a hardness of about Shore 40 D to 75 D, the low durometer plug segment having a hardness of about Shore 55 D to 25 D, the proximal end of the high durometer plug segment being affixed to the distal end of the core wire, the distal end of the high durometer plug segment being affixed to the proximal end of the medium durometer plug segment and the proximal end of the low durometer plug segment being affixed to the distal end of the medium durometer plug segment, the distal end of the tube being affixed to the low durometer plug segment.

11. The guidewire of claim 1 wherein at least one plug segment is loaded with radiopacifier.

12. The guidewire of claim 1 wherein the tip is formed of the distal end of the distal most plug segment.

13. The guidewire of claim 1 having an outer surface with a lubricous coating applied thereto.

14. The guidewire of claim 1 wherein the plug segments are made of thermoplastic.

15. The guidewire of claim 6 wherein the plug segments are made of thermoplastic.

16. The guidewire of claim 12 wherein the tip is free of a spring coil.

17. The guidewire of claim 1 wherein the core wire is made from different material than either the tube or any plug segment.

18. A guidewire for use in a catheter comprising:

an elongate core wire having a uniform outer diameter, a proximal end and a distal end, the distal end of the core wire forms a spherically shaped full radius;

an elongate tube defining a tube lumen, the tube having the same outer diameter as the core wire, the tube having a proximal end and a distal end, the proximal end of the tube being affixed to the distal end of the core wire, the tube having a smooth exterior surface;

two or more plug segments, each plug segment having the same uniform outer diameter as each other along their length, the plug segments filling the tube lumen, each plug segment having a proximal end and a distal end, each plug segment having a stiffness less than that of the core wire and less than that of the proximally preceding plug segment, the proximal end of the proximal most plug segment being affixed to the distal end of the core wire, the distal end of the tube being affixed to the distal most plug segment, the core wire being made from different material than either the tube or any plug segment; and a smoothly rounded distal tip extending beyond and affixed to the distal end of the tube.

19. A guidewire for use in a catheter comprising:

an elongate core wire having a uniform outer diameter, a proximal end and a distal end, the distal end of the core wire forms a spherically shaped full radius;

an elongate metallic tube defining a tube lumen, the tube having the same outer diameter as the core wire, the tube having a proximal end and a distal end, the proximal end of the tube being affixed to the distal end of the core wire, the tube having a smooth exterior surface;

two or more nonmetallic plug segments, each plug segment having the same uniform outer diameter as each other along their length, the plug segments filling the tube lumen, each plug segment having a proximal end and a distal end, each plug segment having a stiffness less than that of the core wire and less than that of the proximally preceding plug segment, the proximal end of the proximal most plug segment being affixed to the distal end of the core wire, the distal end of the tube being affixed to the distal most plug segment; and a smoothly rounded distal tip extending beyond and affixed to the distal end of the tube.

* * * * *